United States Patent
Librizzi et al.

(10) Patent No.: US 11,951,208 B1
(45) Date of Patent: Apr. 9, 2024

(54) LOW IMPACT MANUFACTURING TECHNIQUES FOR THE FORMULATION OF CERAMIDE OIL IN WATER SKIN HEALTH APPLICATIONS

(71) Applicant: The Future Happens Everyday Inc., New York, NY (US)

(72) Inventors: Joseph Librizzi, Hillsborough, NJ (US); Celeste Lee, New York, NY (US); Bryan Taylor, Hillsborough, NJ (US); Lorrie King, New York, NY (US)

(73) Assignee: The Future Happens Everyday Inc., New York, NY (US)

( * ) Notice: Subject to any disclaimer, the term of this patent is extended or adjusted under 35 U.S.C. 154(b) by 0 days.

(21) Appl. No.: 18/120,432

(22) Filed: Mar. 13, 2023

(51) Int. Cl.
*A61K 9/107* (2006.01)
*A61K 31/164* (2006.01)
*A61K 36/899* (2006.01)
*A61K 47/10* (2017.01)
*A61K 47/14* (2017.01)

(52) U.S. Cl.
CPC ............ *A61K 9/107* (2013.01); *A61K 31/164* (2013.01); *A61K 36/899* (2013.01); *A61K 47/10* (2013.01); *A61K 47/14* (2013.01)

(58) Field of Classification Search
None
See application file for complete search history.

(56) References Cited

U.S. PATENT DOCUMENTS 10,980,851 B2 * 4/2021 Osorio ................. A61K 31/164

* cited by examiner

*Primary Examiner* — Jennifer Chin
(74) *Attorney, Agent, or Firm* — Clark G. Sullivan

(57) ABSTRACT

Provided are low impact methods of creating concentrated water-in-oil and oil-in-water nanosized emulsions, effective therapeutic carriers for skin aging preparations. To achieve optimum multifunctional activity, ceramide and plant-based ceramides are selected to naturally mimic epidermal composition; and are made into evenly dispersed, small droplet, high-absorption skincare treatment emulsions. The water-in-oil emulsion is a highly stable, low-water ratio concentrate, of particular benefit to dry and aging skin types. The oil-in-water lipophilic emulsion maximizes lipid and nutrient release into the epidermis (stratum basale to stratum corneum). Lipophilic compositions are non-irritating and highly absorbable, resulting in superior skin health; specifically skin barrier keratinocyte, lipid and hydration improvements and aesthetic improvements, including skin smoothness and wrinkle reduction, while decreasing potential dermatitis and similar. Oil-in-water emulsions are achieved using a novel low-energy, low-cost flip phase methodology, in contrast to hot-stage high pressure homogenization techniques which yield inconsistent droplet sizes and are subject to oxidation.

23 Claims, No Drawings

LOW IMPACT MANUFACTURING TECHNIQUES FOR THE FORMULATION OF CERAMIDE OIL IN WATER SKIN HEALTH APPLICATIONS

FIELD OF THE INVENTION

The present invention relates to ceramide oil in water emulsions and to low impact production methods therefor.

BACKGROUND OF THE INVENTION

Ceramide, a key molecule in sphingolipid metabolism, is composed of a sphingosine base and an amide-linked acyl chain varying in length; the endogenous species most commonly contain fatty acyl groups with 16 to 24 carbon atoms. It is a bioactive sphingolipid linked to induction of senescence, growth inhibition, and cellular apoptosis.

Ceramides serve as both intracellular and intercellular messengers and as regulatory molecules that play essential roles in signal transduction, inflammation, angiogenesis, and metabolic disorders such as diabetes, neurodegenerative diseases, and cancer cell degeneration. Ceramides also play an important structural role in cell membranes by increasing their rigidity, creating micro-domains (rafts and caveolae), and altering membrane permeability; all these events are involved in the cell signaling. Ceramides constitute approximately half of the lipid composition in the human skin contributing to barrier function as well as epidermal signaling as they affect both proliferation and apoptosis of keratinocytes, the major cell type of the epidermis, comprising approximately 90% of the four outer skin layers, from the stratum basale up to stratum corneum. Incorporation of ceramides in topical preparations as functional lipids appears to improve skin barrier functions.

Ceramides used as signaling molecules are synthesized by the SM and catabolic pathways. Synthesized ceramides are released from corneocytes, forming the multilamellar barrier. The major lipids that form the multilamellar barrier of the skin consist of 50% ceramide, 25% cholesterol and 15% fatty acids. Additionally, ceramides and their metabolites regulate the apoptosis, proliferation and differentiation of skin cells as well as the formation and strength of the skin barrier. This creates an epidermal barrier at the level of the stratum corneum, the uppermost layer, to prevent dehydration and moisture loss, common in skin weakened by intrinsic and extrinsic aging factors. The epidermis also prevents external antigens from entering the skin and is a defense against ultraviolet (UV) rays. The epidermal barrier plays key roles in skin aging, psoriasis, dermatitis, and atopic dermatitis.

Ceramides also appear to enhance the bioavailability of drugs by acting as lipid delivery systems. They appear to regulate the inflammatory signaling, and external ceramides have shown relief in the anterior and posterior eye disorders. Ceramides play a structural role in liposome formulations and enhance the cellular uptake of amphiphilic drugs, such as chemotherapies. Unfortunately, the biological utility of ceramide is limited because of its insolubility.

Nano-emulsions and solid lipid nanoparticles are widely used colloidal carriers for bioactive compounds. Nano-emulsions can be formed by using either low or high energy processes. The phase inversion temperature method is a low-energy process based on the changes in solubility of polyoxyethylene type of nonionic surfactants with temperature. These surfactants become lipophilic with increasing temperature because of dehydration of the polyoxyethylene chains. Phase inversion temperature emulsification takes advantage of the extremely low interfacial tensions achieved at inversion temperature. Above this temperature, a water in oil emulsion is formed which becomes a bi-continuous emulsion at the inversion temperature and an oil in water nano-emulsion below.

D phase emulsification is a low-energy process to make nano-emulsions that involves mixing a surfactant with a polyol or with a polyol and a small amount of water. Oil is then added and an oil in water emulsion is typically formed (oil in polyol-water emulsion). When additional water is added, an oil in water nano-emulsion is formed. Heating both phases prior to mixing promotes a smaller particle size due to a lowering of the interfacial tension. The likely mechanism is the formation before dilution of a lamellar liquid crystalline phase.

High-energy approaches use equipment capable of generating intense disruptive forces to break up the oil phases. The most widely used include high-pressure valve homogenizers, micro-fluidizers, and sonication methods. Generally, conventional high-pressure homogenizers work in a range of pressures between 50 and 100 MPa.

What is needed are new methods for topical delivery of ceramides, including ceramide nano-emulsions, and low impact, cost effective methods of making those ceramide nano-emulsions.

SUMMARY OF INVENTION

In a first principal embodiment the invention provides In a first principal embodiment the invention provides a low impact method of making a concentrated, highly absorbable, low-water ratio water in oil (W/O) emulsion comprising one or more ceramides in the oil phase comprising: (a) mixing one or more emulsifiers and one or more glycols at to form an aqueous homogenous mixture comprising water at less than a critical phase inversion concentration than 10 vol. % water; (b) mixing one or more ceramides with the homogeneous mixture to form a water in oil emulsion; and (c) optionally mixing one or more oils with the homogenous mixture, either before, after, or in combination with the ceramides.

In a second principal embodiment the invention provides a low impact methodology to create a highly lipophilic oil in water emulsion for topical delivery of ceramides comprising: (a) an aqueous phase comprising one or more glycols; and (b) an oil phase comprising one or more ceramides and optionally one or more oils; and (c) one or more emulsifiers.

Still further embodiments provide highly lipophilic oil in water emulsions for topical delivery of ceramides comprising: (a) an aqueous phase comprising one or more glycols; and (b) an oil phase comprising one or more ceramides and optionally one or more oils; and (c) one or more emulsifiers.

Additional advantages of the invention are set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

Definitions and Use of Terms

DETAILED DESCRIPTION

As used in this specification and in the claims which follow, the singular forms "a," "an" and "the" include plural referents unless the context clearly dictates otherwise.

As used in this specification and in the claims which follow, the word "comprise" and variations of the word, such as "comprising" and "comprises," means "including but not limited to," and is not intended to exclude, for example, other additives, components, integers or steps. When an element is described as comprising a plurality components, steps or conditions, it will be understood that the element can also be described as comprising any combination of such plurality, or "consisting of" or "consisting essentially of" the plurality or combination of components, steps or conditions.

When ranges are given by specifying the lower end of a range separately from the upper end of the range, or specifying particular numerical values, it will be understood that a range can be defined by selectively combining any of the lower end variables, upper end variables, and particular numerical values that is mathematically possible. In like manner, when a range is defined as spanning from one endpoint to another, the range will be understood also to encompass a span between and excluding the two endpoints.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

The term ceramide refers to a family of waxy lipid molecules, historically composed of N-acetylsphingosine and a fatty acid, including both the naturally occurring epidermal ceramides discussed in Merleev et. al., JCI Insight 2022, and similar compounds derived from plant-based sources such as *Avena sativa* (oat) kernel extract, *Avena sativa* (oat) kernel oil, and *Oryza sativa* (rice) bran oil extract.

DISCUSSION

In a first principal embodiment the invention provides a low impact method of making a concentrated, highly absorbable, low-water ratio water in oil (W/O) emulsion comprising one or more ceramides in the oil phase comprising: (a) mixing one or more emulsifiers and one or more glycols at to form an aqueous homogenous mixture comprising water at less than a critical phase inversion concentration than 10 vol. % water; (b) mixing one or more ceramides with the homogeneous mixture to form a water in oil emulsion; and (c) optionally mixing one or more oils with the homogenous mixture, either before, after, or in combination with the ceramides.

In a second principal embodiment the invention provides a low impact methodology to create an highly lipophilic oil in water emulsion for topical delivery of ceramides comprising: (a) an aqueous phase comprising one or more glycols; (b) an oil phase comprising one or more ceramides and optionally one or more oils; and (c) one or more emulsifiers.

Still further embodiments provide highly lipophilic oil in water emulsions for topical delivery of ceramides comprising: (a) an aqueous phase comprising one or more glycols; and (b) an oil phase comprising one or more ceramides and optionally one or more oils; and (c) one or more emulsifiers.

In one embodiment, the method further comprising converting the water in oil emulsion to an oil in water emulsion comprising the one or more ceramides in the oil phase by combining the water in oil emulsion with sufficient water to form an oil in water emulsion comprising the one or more ceramides in the oil phase.

In one embodiment the homogenous mixture of step (a) comprises less than 5%, 3%, 1%, or 0.5% water.

In one embodiment the ceramides are not present in an oil form, and the one or more oils are mixed with the ceramides prior to step (b).

In another embodiment the water in oil emulsion comprises 10 to 35 weight parts glycols based on 100 weight parts water in oil emulsion.

In another embodiment the one or more glycols are selected from propanediol, propylene glycol, diglycerol, triglycerol, glycerin, and mixtures thereof.

In still another embodiment the water in oil emulsion comprises 20 to 70 weight parts emulsifier based on 100 weight parts water in oil emulsion.

In another embodiment the one or more emulsifiers comprises a polyglyceryl fatty ester, an ethoxylated fatty alcohol, an ethoxylated fatty acid, an ethoxylated sorbitan ester or a mixture thereof.

In another embodiment the one or more emulsifiers comprises a polyglyceryl fatty ester.

In another embodiment the one or more emulsifiers comprises a polyglyceryl fatty ester derived from (a) a polyglycerol component built up from 2 molecules to 12 molecules of glycerin, based on an average, and (b) a fatty acid selected from caprylic acid, capric acid, lauric acid, myristic acid, palmitic acid, stearic acid, arachidic acid, behenic acid, lignoceric acid, cerotic acid, oleic acid, decaoleic acid and mixtures thereof.

In another embodiment the one or more emulsifiers comprises a polyglyceryl fatty ester selected from polyglyceryl-10 decaoleate; polyglyceryl-3 stearate; polyglyceryl-10 stearate; polyglyceryl-10 oleate; polyglyceryl-10 caprylate/caprate; and mixtures thereof.

In still another embodiment the one or more emulsifiers are selected from polyglyceryl-10 oleate and peg-20 glyceryl triisostearate.

In another embodiment the water in oil emulsion comprises 0.1 to 50 weight parts ceramides based on 100 weight parts water in oil emulsion.

In another embodiment the ceramides are selected from *Avena sativa* (oat) kernel extract, *Avena sativa* (oat) kernel oil, and *Oryza sativa* (rice) bran oil extract.

In another embodiment the water in oil emulsion comprises 0.1 to 5 weight parts ceramides based on 100 weight parts water in oil emulsion when the ceramides are not used in an oil form.

In another embodiment the water in oil emulsion comprises 0.5 to 50 weight parts ceramides based on 100 weight parts water in oil emulsion when the ceramides are used in an oil form.

In another embodiment the water in oil emulsion comprises 10 to 35 weight parts oils based on 100 weight parts water in oil emulsion.

In another embodiment the water in oil emulsion comprises 10 to 35 weight parts oils based on 100 weight parts water in oil emulsion, and the ceramides are not used in an oil form.

In another embodiment the one or more oils are selected from ester oil, an ether oil, and mixtures thereof.

In another embodiment the one or more oils comprises a dialkyl carbonate.

In another embodiment the one or more oils comprises a dialkyl carbonate selected from dicaprylyl carbonate, ethylhexyl carbonate, dihexyl carbonate and mixtures thereof.

In another embodiment the one or more oils are selected from dodecane, caprylic/capric triglycerides, and squalane.

In another embodiment the oil in water emulsion comprises: (a) from 50 to 90 weight parts water in oil emulsion; and (b) from 10 to 50 weight parts water; based on 100 weight parts oil in water emulsion.

In another embodiment In one embodiment, the oil in water emulsion is in the form of a topical cream, gel, lotion, liquid, or foam, further comprising one or more topical excipients.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Three experiments were conducted to evaluate the effect of ceramide, emulsifier, and glycol on the formation of a water in oil emulsion concentrate. The process for making the concentrate was as follows: In the main beaker, add the surfactant. Under slight heating (up to 50° C.) and agitation, add the glycol. Once homogenous, remove from heat and add the natural ceramide. If an oil is used, pre-mix the natural ceramide with the oil then add the mixture into the main vessel under agitation. Continue mixing until the batch cools to room temperature.

Table 1a reports various natural ceramides tested as individual ceramides or blends of ceramides. The three ceramides used were *Avena sativa* (oat) kernel extract, *Avena sativa* (oat) kernel oil, and *Oryza sativa* (rice) bran oil extract. For all formulations, the concentrate formed a milky white mixture when introduced to water under agitation, visually confirming that an emulsion has formed.

TABLE 1a

Varying Ceramides

|  | Exp#1 | Exp#2 | Exp#3 | Exp#4 | Exp#10 |
|---|---|---|---|---|---|
| Polyglyceryl-10 Oleate | 47.62% | 47.62% | 47.62% | 47.62% | 47.62% |
| Propanediol | 25.64% | 25.64% | 25.64% | 25.64% | 25.64% |
| Dodecane | 25.74% | 25.74% | — | 25.74% | 25.74% |
| Avena Sativa (Oat) Kernel Extract | 1.00% | — | — | — | 0.50% |
| Avena Sativa (Oat) Kernel Oil | — | 1.00% | 26.74% | — | 0.50% |
| Oryza Sativa (Rice) Bran Oil Extract | — | — | — | 1.00% | — |

Various emulsifiers were also tested as individual emulsifiers or a blend of emulsifiers, as reported in Table 1b. The two emulsifiers used were polyglyceryl-10 oleate and PEG-20 glyceryl triisostearate. Once again, for all formulations, the concentrate formed a milky white mixture when introduced to water under agitation, visually confirming that an emulsion had formed.

TABLE 1b

Varying Emulsifiers

|  | Exp#4 | Exp#5 | Exp#6 | Exp#8 | Exp#11 | Exp#12 | Exp#13 |
|---|---|---|---|---|---|---|---|
| Polyglyceryl-10 Oleate | 47.62% | 47.62% | 47.62% | — | 32.62% | — | — |
| PEG-20 Glyceryl Triisostearate | — | — | — | 47.62% | 15.00% | 47.62% | 47.62% |
| Propanediol | 25.64% | 25.64% | 25.64% | 25.64% | 25.64% | — | 25.64% |
| Glycerin | — | — | — | — | — | 25.64% | — |
| Dodecane | 25.74% | — | — | 25.74% | 25.74% | — | — |
| Caprylic/Capric Triglycerides | — | 25.74% | — | — | — | 25.74% | — |
| Squalane | — | — | 25.74% | — | — | — | 25.74% |
| Avena Sativa (Oat) Kernel Extract | — | 1.00% | — | — | 1.00% | — | — |
| Avena Sativa (Oat) Kernel Oil | — | — | — | — | — | 1.00% | — |
| Oryza Sativa (Rice) Bran Oil Extract | 1.00% | — | 1.00% | 1.00% | — | — | 1.00% |

Various glycols were also tested, as reported in Table 1c. The glycols used were propanediol, propylene glycol, and glycerin. The glycol is used to starve the emulsifier of water, thereby forcing the emulsifier into an unfavorable state. Once again, for all formulations, the concentrate formed a milky white mixture when introduced to water under agitation, visually confirming that an emulsion has formed.

TABLE 1c

Varying Glycols

|  | Exp#2 | Exp#7 | Exp#9 | Exp#12 |
|---|---|---|---|---|
| Polyglyceryl-10 Oleate | 47.62% | 47.62% | 47.62% | — |
| PEG-20 Glyceryl Triisostearate | — | — | — | 47.62% |
| Propanediol | 25.64% | — | — | — |
| Propylene Glycol | — | 25.64% | — | — |
| Glycerin | — | — | 25.64% | 25.64% |
| Dodecane | 25.74% | 25.74% | — | — |
| Caprylic/Capric Triglycerides | — | — | 25.74% | 25.74% |
| Avena Sativa (Oat) Kernel Extract | — | 1.00% | — | — |
| Avena Sativa (Oat) Kernel Oil | 1.00% | — | 1.00% | 1.00% |

Particle size diameters were measured for the oil in water emulsions formed when the concentrates were added to water. The tests were run on a Horiba LA950-V2 Partica analyzer (light microscopy) using the wet cell module with water as the dispersion solvent. Because the samples were concentrates which were intended to form emulsions when added to water, samples were prepared by directly adding small droplets of the sample using a pipette. The number of drops and machine response varied greatly between samples, but the minimum number of drops was added which allowed the system to operate within the recommended transmittance windows.

The system was aligned and calibrated to the circulating water bath before each sample set was measured. The sample was introduced into the bath dropwise. The sample was then subjected to a 30-second burst of ultrasonic energy using the internal ultrasonic horn. Once reasonable stability was noted, indicated by a settled response in the real-time histogram, a measurement of the particle size distribution was then taken. Where possible, three measurements were conducted on the sample to assure repeatability. After the third measurement, the data was checked for consistency and if reasonable, an average data set for the three runs was calculated and the graphic report was generated for a given sample. The system was then flushed and the process repeated for the next sample.

The emulsions described in the foregoing examples can be converted made into a finished moisturizing composition according to the following steps:

In the main vessel, pre-mix Propanediol with Phase A.
Add Water under agitation to the pre-mix.
Begin heating the main vessel to 75 C
In a side vessel, add Phase B and begin heating to 75 C
At temperature, add Phase B into the main vessel containing Phase A
Remove from heat, continue mixing
At room temperature, add Phase C stepwise into the main vessel
Adjust pH and q.s. with water.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A low impact method of making a highly absorbable, concentrated water in oil (W/O) emulsion comprising one or more ceramides in the oil phase comprising:
    a. mixing one or more emulsifiers and one or more glycols to form an aqueous homogenous mixture comprising water at less than a critical phase inversion concentration of 10 vol. % water;
    b. mixing one or more ceramides with the homogeneous mixture to form a water in oil emulsion; and
    c. optionally mixing one or more oils with the homogenous mixture, either before, after, or in combination with the ceramides.

2. The method of claim 1, further comprising a low impact method converting the water in oil emulsion to a highly lipophilic oil in water emulsion comprising the one or more ceramides in the oil phase by combining the water in oil emulsion with sufficient water to form an oil in water emulsion comprising the one or more ceramides in the oil phase.

3. The method of claim 1, wherein the homogenous mixture of step (a) comprises less than 5%, 3%, 1%, or 0.5% water.

4. The method of claim 1, wherein the ceramides are not present in an oil form, and the one or more oils are mixed with the ceramides prior to step (b).

5. The method of claim 1, wherein the water in oil emulsion comprises 10 to 35 weight parts glycols based on 100 weight parts water in oil emulsion.

6. The method of claim 1, wherein the one or more glycols are selected from propanediol, propylene glycol, diglycerol, triglycerol, glycerin, and mixtures thereof.

7. The method of claim 1, wherein the water in oil emulsion comprises 20 to 70 weight parts emulsifier based on 100 weight parts water in oil emulsion.

8. The method of claim 1, wherein the one or more emulsifiers comprises a polyglyceryl fatty ester, an ethoxylated fatty alcohol, an ethoxylated fatty acid, an ethoxylated sorbitan ester or a mixture thereof.

9. The method of claim 1, wherein the one or more emulsifiers comprises a polyglyceryl fatty ester.

10. The method of claim 1, wherein the one or more emulsifiers comprises a polyglyceryl fatty ester derived from (a) a polyglycerol component built up from 2 molecules to 12 molecules of glycerin, based on an average, and (b) a fatty acid selected from caprylic acid, capric acid, lauric acid, myristic acid, palmitic acid, stearic acid, arachidic acid, behenic acid, lignoceric acid, cerotic acid, oleic acid, decaoleic acid and mixtures thereof.

11. The method of claim 1, wherein the one or more emulsifiers comprises a polyglyceryl fatty ester selected from polyglyceryl-10 decaoleate; polyglyceryl-3 stearate; polyglyceryl-10 stearate; polyglyceryl-10 oleate; polyglyceryl-10 caprylate/caprate; and mixtures thereof.

12. The method of claim 1, wherein the one or more emulsifiers are selected from polyglyceryl-10 oleate and peg-20 glyceryl triisostearate.

13. The method of claim 1, wherein the water in oil emulsion comprises 0.1 to 50 weight parts ceramides based on 100 weight parts water in oil emulsion.

14. The method of claim 1, wherein the ceramides are selected from *Avena sativa* kernel extract, *Avena sativa* kernel oil, and *Oryza sativa* bran oil extract.

15. The method of claim 1, wherein the water in oil emulsion comprises 0.1 to 5 weight parts ceramides based on 100 weight parts water in oil emulsion when the ceramides are not used in an oil form.

16. The method of claim 1, wherein the water in oil emulsion comprises 0.5 to 50 weight parts ceramides based on 100 weight parts water in oil emulsion when the ceramides are used in an oil form.

17. The method of claim 2, wherein the water in oil emulsion comprises 10 to 35 weight parts oils based on 100 weight parts water in oil emulsion.

18. The method of claim 2, wherein the water in oil emulsion comprises 10 to 35 weight parts oils based on 100 weight parts water in oil emulsion, and the ceramides are not used in an oil form.

19. The method of claim 2, wherein the one or more oils are mixed with the homogenous mixture, and the one or more oils are selected from ester oil, an ether oil, and mixtures thereof.

20. The method of claim 2, wherein the one or more oils are mixed with the homogenous mixture, and the one or more oils comprises a dialkyl carbonate.

21. The method of claim 2, wherein the one or more oils are mixed with the homogenous mixture, and the one or more oils comprises a dialkyl carbonate selected from dicaprylyl carbonate, ethylhexyl carbonate, dihexyl carbonate and mixtures thereof.

22. The method of claim 2, wherein the one or more oils are mixed with the homogenous mixture, and the one or more oils are selected from dodecane, caprylic/capric triglycerides, and squalane.

23. The method of claim 3, wherein the oil in water emulsion comprises:
  a. from 50 to 90 weight parts water in oil emulsion; and
  b. from 10 to 50 weight parts water;
  based on 100 weight parts oil in water emulsion.

\* \* \* \* \*